United States Patent
Lin et al.

(10) Patent No.: US 11,839,640 B2
(45) Date of Patent: Dec. 12, 2023

(54) PREBIOTIC COMPOSITION AND METHODS FOR USING THE SAME

(71) Applicant: TCI CO., LTD., Taipei (TW)

(72) Inventors: Yung-Hsiang Lin, Taipei (TW); Chu-Han Huang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/674,834

(22) Filed: Feb. 17, 2022

(65) Prior Publication Data

US 2023/0233643 A1    Jul. 27, 2023

(30) Foreign Application Priority Data

Jan. 27, 2022   (TW) ................................ 111103772

(51) Int. Cl.
*A61K 36/87* (2006.01)
*A61K 31/702* (2006.01)
*A61K 31/7032* (2006.01)
*A61P 1/14* (2006.01)
*A61K 31/733* (2006.01)

(52) U.S. Cl.
CPC ............ *A61K 36/87* (2013.01); *A61K 31/702* (2013.01); *A61K 31/7032* (2013.01); *A61K 31/733* (2013.01); *A61P 1/14* (2018.01); *A61K 2236/19* (2013.01)

(58) Field of Classification Search
None
See application file for complete search history.

(56) References Cited

U.S. PATENT DOCUMENTS

2013/0171204 A1*   7/2013   DuBourdieu .......... A23K 40/25
                                                  426/71

OTHER PUBLICATIONS

Roopchand et al. "Dietary Polyphenols Promote Growth of the Gut Bacterium *Akkermansia muciniphila* and Attenuate High-Fat Diet-Induced Metabolic Syndrome". Diabetes, Aug. 2015; vol. 64, pp. 2847-2858.*
Wang et al. "Effects of probiotics and prebiotics on intestinal microbiota in mice with acute colitis based on 16S rRNA gene sequencing". Chinese Medical Journal. 2019, 132(15), pp. 1833-1842.*
Zhou et al. Frontiers in Microbiology, Feb. 2021, vol. 12, article 635333, pp. 1-15.*
Ying Shi et al. Restoration of cefixime-induced gut microbiota changes by Lactobacillus cocktails and fructooligosaccharides in a mouse model. Microbiological Research, 2017, 200, pp. 14-24.*
Mechanisms of Action of Prebiotics and Their Effects on Gastro-Intestinal Disorders in Adults., Michele Pier Luca Guarino et al., Nutrients 2020, 12, 1037, Apr. 9, 2020 Full text, abstract, pp. 8-9.

* cited by examiner

*Primary Examiner* — Vera Afremova
(74) *Attorney, Agent, or Firm* — Chieh-Mei Wang

(57) ABSTRACT

Prebiotic composition including grape ferment, a first component, and a second component is provided. The first component is lactitol or xylooligosaccharide, and the second component is fructooligosaccharide, xylooligosaccharide, or inulin. The first component is different from the second component, and a weight ratio of the grape ferment, the first component and the second component falls within the range of 1-2:1-2:1-2. Based on this, the prebiotic composition prepared by grape ferment can be used to promote intestinal health of a subject in need thereof and enhance antioxidation in the subject.

4 Claims, 3 Drawing Sheets

PREBIOTIC COMPOSITION AND METHODS FOR USING THE SAME

CROSS-REFERENCE TO RELATED APPLICATION

This non-provisional patent application claims priority under 35 U.S.C. § 119(a) to Patent Application No. 111103772 filed in Taiwan, R.O.C. on Jan. 27, 2022, the entire contents of which are hereby incorporated by reference.

BACKGROUND

Technical Field

The present invention relates to use of a prebiotic composition. Grape ferment is used to prepare the prebiotic composition, and the prebiotic composition is used to promote intestinal health of a subject in need thereof and enhance antioxidation in the subject.

Related Art

Prebiotics are polysaccharides in natural food and are not easily digested by human enzymes, but they can be utilized by probiotics in the digestive system (mainly large intestine) to generate short chain fatty acids (SFCAs) by growth, expansion and metabolism in the flora.

According to the consensus statement of International Scientific Association for Probiotics and Prebiotics (ISAPP) on prebiotics in *Nature report* 2017, the prebiotic is defined as "a substrate that is selectively utilized by host microorganisms conferring a health benefit."

Specifically, prebiotics can help probiotics grow and help to inhibit bad bacteria in the intestinal tract. The probiotics in the intestinal tract also metabolize prebiotics into short chain fatty acids, and the short chain fatty acids are then provided to the probiotics and the host as an energy source.

SUMMARY

In view of this, the present invention provides a prebiotic composition, including grape ferment. The prebiotic composition is used to promote growth of *Akkermansia muciniphila* and can be used to promote intestinal health of a subject and/or enhance antioxidation in the subject.

In some embodiments, the prebiotic composition includes grape ferment, a first component and a second component. The first component is lactitol or xylooligosaccharide, and the second component is fructooligosaccharide, xylooligosaccharide, or inulin. The first component is different from the second component. A weight ratio of the grape ferment, the first component and the second component falls within a range of 1-2:1-2:1-2.

In some embodiments, the weight ratio of the grape ferment, the first component and the second component included in the prebiotic composition is 2:1:1.

In some embodiments, the prebiotic composition is used to promote growth of *Akkermansia muciniphila*.

In some embodiments, the prebiotic composition includes the grape ferment, the lactitol as the first component, and the fructooligosaccharide as the second component.

In some embodiments, provided is a method for promoting intestinal health of a subject in need thereof, including administering to the subject a prebiotic composition. The prebiotic composition includes grape ferment, lactitol, and fructooligosaccharide. A weight ratio of the grape ferment, the lactitol, and the fructooligosaccharide falls within a range of 1-2:1-2:1-2.

In some embodiments, provided is use of grape ferment in preparation of a prebiotic composition for promoting intestinal health of a subject. The prebiotic composition includes the grape ferment, lactitol, and fructooligosaccharide. A weight ratio of the grape ferment, the lactitol, and the fructooligosaccharide falls within a range of 1-2:1-2:1-2.

In some embodiments, promoting intestinal health of the subject includes promoting growth of probiotics, and the probiotics include *Akkermansia muciniphila* and *Bifidobacterium*.

In some embodiments, the prebiotic composition is used to promote growth of *Akkermansia muciniphila*.

In some embodiments, provided is a method for enhancing antioxidation in a subject in need thereof, including administering to the subject a prebiotic composition. The prebiotic composition includes grape ferment, lactitol, and fructooligosaccharide. A weight ratio of the grape ferment, the lactitol, and the fructooligosaccharide falls within a range of 1-2:1-2:1-2.

In some embodiments, provided is use of grape ferment in preparation of a prebiotic composition for enhancing antioxidation in a subject. The prebiotic composition includes the grape ferment, lactitol, and fructooligosaccharide. A weight ratio of the grape ferment, the lactitol, and the fructooligosaccharide falls within a range of 1-2:1-2:1-2.

In some embodiments, the prebiotic composition is used to increase contents of sulfur compounds and total glutathione in the subject.

In some embodiments, the sulfur compounds are thiols.

In some embodiments, the weight ratio of the grape ferment, the lactitol, and the fructooligosaccharide included in the prebiotic composition is 2:1:1.

Based on the above, the prebiotic composition according to any of the embodiments includes the grape ferment, the first component, and the second component. The first component is lactitol or xylooligosaccharide, and the second component is fructooligosaccharide, xylooligosaccharide, or inulin. In addition, the prebiotic composition is used to promote growth of *Akkermansia muciniphila*. In some embodiments, the grape ferment can be used to prepare a prebiotic composition for promoting intestinal health of the subject and/or enhancing antioxidation in the subject, and the prebiotic composition includes the grape ferment, lactitol, and fructooligosaccharide. In some embodiments, the prebiotic composition can promote growth of probiotics. For example, the probiotics include *Akkermansia muciniphila* and *Bifidobacterium*. In some embodiments, the prebiotic composition can increase the contents of sulfur compounds (such as thiols) and total glutathione in the subject.

DETAILED DESCRIPTION

Figure 1:
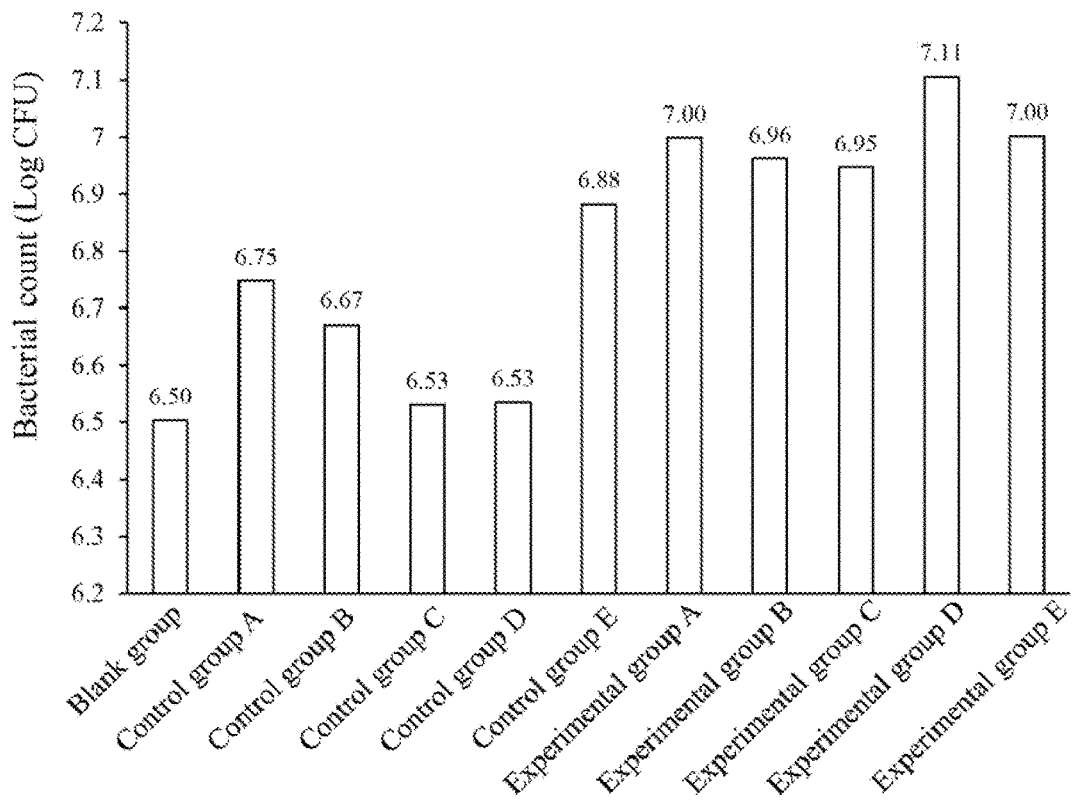
FIG. 1 is a graph showing experimental results of analysis on the effects of prebiotic compositions with different components on probiotics in multiple groups.

A prebiotic composition including grape ferment, sugar alcohols or saccharides as a first component, and saccharides as a second component. The first component is different from the second component. The sugar alcohols may be lactitol, and the saccharides may be oligosaccharides, dietary fibers and other polysaccharides, such as xylooligosaccharide, fructooligosaccharide and inulin. Besides, the grape ferment is prepared by fermenting a grape extract prepared from red grape fruits under the actions of yeast and *Lactobacillus*.

In some embodiments, the prebiotic composition includes the grape ferment, lactitol, and a polysaccharide. A weight ratio of the grape ferment, the lactitol, and the polysaccharide falls within a range of 1-2:1-2:1-2. The polysaccharide may be fructooligosaccharide, xylooligosaccharide, or inulin. For example, the weight ratio of the grape ferment, the lactitol, and the polysaccharide is 2:1:1.

In some embodiments, the prebiotic composition includes the grape ferment, xylooligosaccharide and a polysaccharide. A weight ratio of the grape ferment, the xylooligosaccharide and the polysaccharide falls within a range of 1-2:1-2:1-2. The polysaccharide may be fructooligosaccharide or inulin. For example, the weight ratio of the grape ferment, the xylooligosaccharide and the polysaccharide is 2:1:1.

In some implementations, the prebiotic composition includes the grape ferment, lactitol, and fructooligosaccharide. A weight ratio of the grape ferment, the lactitol, and the fructooligosaccharide falls within a range of 1-2:1-2:1-2. For example, the prebiotic composition includes the grape ferment, lactitol, and fructooligosaccharide in the weight ratio of 2:1:1.

In some embodiments, a preparation process of the grape ferment includes: preparing a grape extract, inoculating a plurality of strains into the grape extract, and carrying out static culture.

The grape extract may be red grape juice obtained by squeezing red grape (*Vitis vinifera*) fruits, or concentrated grape juice obtained by concentrating the red grape juice, or a grape juice dilution obtained by diluting the red grape juice or the concentrated grape juice, or a grape juice obtained by extracting red grape fruits with a solvent.

For example, the red grape fruits are directly mashed and filtered to obtain the grape extract. In some embodiments, the red grape fruits include peel, pulp and seeds. In some embodiments, the grape extract may be prepared by blending commercially available concentrated grape juice and water. In some embodiments, the grape extract may be prepared by blending concentrated grape juice, water and glucose. In some embodiments, the grape extract may be prepared by heating concentrated grape juice, water and glucose to 95° C. or above and holding for 30 minutes. A volume ratio of the concentrated grape juice to the water may be 1:8. Besides, a concentration of the glucose may be 3% (W/V), or an amount of the glucose is added such that the ° Brix of the grape extract is greater than or equal to 8. That is, while adding the glucose, the ° Brix of the solution is measured synchronously, and when the ° Brix of the grape extract reaches 8 or exceeds 8, the addition of the glucose is stopped. In some embodiments, the red grapes may be Sangiovese or Lambrusco red grapes, or a mixture thereof.

The plurality of strains include yeast and *Lactobacillus*.

In some embodiments, the grape ferment may be prepared by inoculating 0.1% (W/V) yeast and 0.05% (W/V) *Lactobacillus* into the grape extract and carrying out static culture. In some embodiments, the grape ferment may be prepared by carrying out static culture on a grape extract mixed with 0.1% (W/V) yeast and 0.05% (W/V) *Lactobacillus* and then carrying out vacuum concentration and/or filtration. In other words, the grape ferment may be a primary solution obtained by culturing the grape extract and the plurality of strains, a concentrated solution obtained by carrying out vacuum concentration on the primary solution, a filtrate obtained by filtering the primary solution, or a concentrated filtrate obtained by carrying out vacuum concentration and filtration on the primary solution.

A culture time of the grape extract and the plurality of strains may be 72 hours. Furthermore, a culture temperature of the grape extract and the plurality of strains may be 30° C.

A temperature during the vacuum concentration may be 55° C.-65° C.

The yeast may be *Saccharomyces cerevisiae*. For example, the *Saccharomyces cerevisiae* may be a *Saccharomyces cerevisiae* strain deposited in Bioresource Collection and Research Center (BCRC) of the Food Industry Research and Development Institute with the Deposit Number BCRC20271 (also deposited in DSMZ with the International Deposit Number ATCC33107), or other commercially available *Saccharomyces cerevisiae* strains.

The *Lactobacillus* may be *Streptococcus thermophilus*, *Lactobacillus helveticus* or *Lactobacillus plantarum*. For example, the *Lactobacillus* may be *Streptococcus thermophilus* TC1633 deposited in BCRC with the Deposit Number BCRC910636 (also deposited in DSMZ with the International Deposit Number DSM28121), *Lactobacillus helveticus* TC1357 deposited in BCRC with the Deposit Number BCRC910846 (also deposited in DSMZ with the International Deposit Number DSM33107), *Streptococcus thermophilus* TCI028 with the Deposit Number BCRC910805 (also deposited in DSMZ with the International Deposit Number DSM33108), *Streptococcus thermophilus* TC1378 with the Deposit Number BCRC910760 (also deposited in DSMZ with the International Deposit Number DSM32451), other commercially available *Streptococcus thermophilus* strains, other commercially available *Lactobacillus helveticus* strains, or other commercially available *Lactobacillus plantarum* strains.

For example, concentrated juice of red grapes and water are blended to obtain a grape juice solution. A volume ratio of the concentrated juice to the water is 1:8. Next, 3% (W/V) glucose is added to the grape juice solution, and the mixture is allowed to stand at 95° C. for 0.5 hour to obtain a grape extract. Then, 0.1% (W/V) *Saccharomyces cerevisiae* and 0.05% (W/V) *Streptococcus thermophilus* TCI633 are inoculated into the obtained grape extract and subjected to static culture at 30° C. for 72 hours to obtain a grape fermentation primary solution. Next, the grape fermentation primary solution is subjected to vacuum concentration at 60° C., and the grape fermentation primary solution subjected to vacuum concentration is filtered through a filter screen with a pore size of 400 mesh to obtain the grape ferment.

Based on this, the grape ferment obtained by the specific process, the lactitol or xylooligosaccharide as the first component, and the fructooligosaccharide, xylooligosaccharide, or inulin as the second component are mixed in a specific ratio to obtain the prebiotic composition. The weight ratio of the grape ferment, the first component and the second component falls within a range of 1-2:1-2:1-2. Besides, the prebiotic composition can increase the bacterial count of probiotics (such as *Akkermansia muciniphila*) in the intestinal tract of a subject.

In some embodiments, the prebiotic composition including the grape ferment, the lactitol, and the fructooligosaccharide can be used to promote intestinal health of a subject. For example, the prebiotic composition can increase the bacterial count of the *Akkermansia muciniphila* in the intestinal tract of the subject by at least 2.5 folds and the bacterial count of the *Bifidobacterium* by at least 3.8 folds. Thereby, the prebiotic composition can improve the intestinal microbiota, thereby achieving the effect of promoting intestinal health of the subject.

In some embodiments, the prebiotic composition including the grape ferment, the lactitol, and the fructooligosaccharide can enhance antioxidation in the subject. For example, the prebiotic composition can increase the content of sulfur compounds, the content of total glutathione or a combination thereof in the body of the subject. In some embodiments, the sulfur compounds are thiols. By increasing the sulfur compounds and/or the total glutathione, the subject's ability of scavenging free radicals can be increased, thereby enhancing the defense against oxidative stress on cells.

In some embodiments, the prebiotic composition may be solid, for example, powder, a tablet and a capsule.

In some embodiments, a dose of the prebiotic composition is 400 mg/day. For example, the prebiotic composition is mainly composed of the grape ferment, the lactitol, and the fructooligosaccharide, and the daily dose 400 mg of the prebiotic composition means that a total dose of the grape ferment, the lactitol, and the fructooligosaccharide is 400 mg.

Any of the aforementioned prebiotic compositions may be a pharmaceutical. In other words, the pharmaceutical includes effective contents of the grape ferment, the lactitol, or the xylooligosaccharide as the first component, and the fructooligosaccharide, the xylooligosaccharide or the inulin as the second component in a specific ratio.

In some embodiments, the aforementioned pharmaceutical can be manufactured into dosage forms suitable for being enterally, parenterally, orally or topically administered using techniques well known to those skilled in the art.

In some embodiments, the enterally or orally administered dosage forms may be, but not limited to, tablets, troches, lozenges, pills, capsules, dispersible powder or granules, solutions, suspensions, emulsions, syrup, elixir, slurry or the like. In some embodiments, the parenterally or topically administered dosage forms may be, but not limited to, injections, sterile powder, external preparations or the like. In some embodiments, the injections may be administered by subcutaneous injection, intraepidermal injection, intradermal injection or intralesional injection.

In some embodiments, the aforementioned pharmaceutical may include a pharmaceutically acceptable carrier widely used in pharmaceutical manufacturing techniques. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome and the like. The type and quantity of carriers to be used are within the professional quality and routine skill of those skilled in the art. In some embodiments, the solvent used as a pharmaceutically acceptable carrier may be water, normal saline, phosphate buffered saline (PBS), or an aqueous solution containing alcohol.

In some embodiments, any of the aforementioned prebiotic compositions may be an edible product. In other words, the edible product includes specific contents of the grape ferment, the lactitol, or the xylooligosaccharide as the first component, and the fructooligosaccharide, the xylooligosaccharide or the inulin as the second component in a specific ratio. In some embodiments, the edible product may be a general food, a health food or a dietary supplement.

In some embodiments, the aforementioned edible product may be manufactured into dosage forms suitable for being orally administered using techniques well known to those skilled in the art. In some embodiments, the aforementioned general food may be the edible product itself. In some embodiments, the general food may be, but not limited to, beverages, fermented foods, bakery products or seasonings.

In some embodiments, the obtained prebiotic composition can be further used as a food additive to obtain a food composition containing the prebiotic composition composed of the grape ferment, the lactitol, or the xylooligosaccharide as the first component, and the fructooligosaccharide, the xylooligosaccharide or the inulin as the second component in a specific ratio. The edible product (i.e. food composition) for ingestion by humans and non-human animals can be prepared from any edible material by adding the prebiotic composition of any embodiment during the preparation of raw materials or by adding the prebiotic composition of any embodiment during the production of food by conventional methods.

Example 1: Preparation of Grape Ferment

First, concentrated juice of Italian Sangiovese red grapes and water were blended to obtain a grape juice solution. A volume ratio of the concentrated juice to the water was 1:8. The concentrated juice was purchased from the supplier Diana Food, and the product number was CC01460001.

Next, 3% (W/V) glucose was added to the grape juice solution, and the mixture was allowed to stand at 95° C. for 0.5 hour to obtain a grape extract. Then, 0.1% (W/V) *Saccharomyces cerevisiae* with the Deposit Number BCRC20271 and 0.05% (W/V) *Streptococcus thermophilus* TC1633 with the Deposit Number BCRC910636 were inoculated into the grape extract and subjected to static culture at 30° C. for 72 hours to obtain a grape fermentation primary solution. The ° Brix of the grape fermentation primary solution was 4.0±0.5 (20° C.), and the pH was 3.0±0.5.

Then, the grape fermentation primary solution was subjected to vacuum concentration at about 60° C., and then filtered through a filter screen with a pore size of 400 mesh to obtain the grape ferment.

Example 2: Effects of Prebiotic Compositions with Different Components on Probiotics The xylooligosaccharide used was purchased from Shandong Longlive Bio-Technology Co., Ltd. The lactitol used was purchased from Welltech Biotechnology Co., Ltd. The inulin used was purchased from Cosucra. The fructooligosaccharide used was purchased from Meiji. The grape ferment used was the grape ferment prepared in Example 1.

The liquid medium used was tryptone soy broth (TSB; hereinafter referred to as TSB medium) with 5% sheep blood (purchased from BD).

The groups were divided into blank group, 5 experimental groups (experimental groups A-E) and 5 control groups (control groups A-E), as shown in Table 1.

TABLE 1

| Group | Components of medium | Components of prebiotic composition |
|---|---|---|
| Blank group | 95% TSB medium + 5% sheep blood | None |
| Control group A | 94% TSB medium + 5% sheep blood + 1% prebiotic composition A | 100% xylooligosaccharide |
| Control group B | 94% TSB medium + 5% sheep blood + 1% prebiotic composition B | 100% lactitol |
| Control group C | 94% TSB medium + 5% sheep blood + 1% prebiotic composition C | 100% inulin |
| Control group D | 94% TSB medium + 5% sheep blood + 1% prebiotic composition D | 100% fructooligosaccharide |
| Control group E | 94% TSB medium + 5% sheep blood + 1% prebiotic composition E | 100% grape ferment |
| Experimental group A | 94% TSB medium + 5% sheep blood + 1% prebiotic composition F | 50% grape ferment + 25% xylooligosaccharide + 25% lactitol (in a weight ratio of 2:1:1) |
| Experimental group B | 94% TSB medium + 5% sheep blood + 1% prebiotic composition G | 50% grape ferment + 25% xylooligosaccharide + 25% fructooligosaccharide (in a weight ratio of 2:1:1) |
| Experimental group C | 94% TSB medium + 5% sheep blood + 1% prebiotic composition H | 50% grape ferment + 25% xylooligosaccharide + 25% inulin (in a weight ratio of 2:1:1) |
| Experimental group D | 94% TSB medium + 5% sheep blood + 1% prebiotic composition I | 50% grape ferment + 25% lactitol + 25% fructooligosaccharide (in a weight ratio of 2:1:1) |
| Experimental group E | 94% TSB medium + 5% sheep blood + 1% prebiotic composition J | 50% grape ferment + 25% lactitol + 25% inulin (in a weight ratio of 2:1:1) |

As shown in Table 1, the experimental medium used in the blank group was liquid culture medium (i.e. 95% TSB medium and 5% sheep blood). The experimental medium used in control groups A-E included 94% TSB medium, 5% sheep blood and 1% single-component prebiotic compositions A-E, respectively; and the single-component prebiotic compositions A-E were xylooligosaccharide, lactitol, inulin, fructooligosaccharide and grape ferment, respectively. The experimental medium used in experimental groups A-E included 94% TSB medium, 5% sheep blood and 1% prebiotic compositions F-J with different components. The prebiotic composition F included grape ferment, xylooligosaccharide, and lactitol in a weight ratio of 2:1:1. The prebiotic composition G included grape ferment, xylooligosaccharide, and fructooligosaccharide in a weight ratio of 2:1:1. The prebiotic composition H included grape ferment, xylooligosaccharide, and inulin in a weight ratio of 2:1:1. The prebiotic composition 1 included grape ferment, lactitol, and fructooligosaccharide in a weight ratio of 2:1:1. The prebiotic composition J included grape ferment, lactitol, and inulin in a weight ratio of 2:1:1.

1% activated *Akkermansia muciniphila* was respectively added to a 15 mL test tube containing 5 mL of medium of each group, and subjected to anaerobic culture at 37° C. for 48 hours. After 48 hours of culture, 100 µL of bacterial suspension was respectively taken from the test tube of each group, added to the solid TSB medium containing 5% sheep blood, and subjected to anaerobic culture at 37° C. for 72 hours, and then, the bacterial count of each group was calculated. The bacterial count was expressed by colony-forming unit (CFU).

Referring to FIG. 1, the bacterial count of the blank group was 6.50 log CFU, the bacterial count of control group A was 6.75 log CFU, the bacterial count of control group B was 6.67 log CFU, the bacterial count of control group C was 6.53 log CFU, the bacterial count of control group D was 6.53 log CFU, the bacterial count of control group E was 6.88 log CFU, the bacterial count of experimental group A was 7.00 log CFU, the bacterial count of experimental group B was 6.96 log CFU, the bacterial count of experimental group C was 6.95 log CFU, the bacterial count of experimental group D was 7.11 log CFU, and the bacterial count of experimental group E was 7.00 log CFU.

As shown in FIG. 1, as compared with the blank group, in the single-component prebiotic compositions, the grape ferment, the xylooligosaccharide and the lactitol increased the bacterial count of *Akkermansia muciniphila*, and the inulin and the fructooligosaccharide have no significant effects on promoting growth of *Akkermansia muciniphila*.

In addition, after these prebiotic components are prepared from the grape ferment, as compared with the blank group, the prebiotic compositions composed of multiple components promoted the growth of *Akkermansia muciniphila* and increased the bacterial count of *Akkermansia muciniphila*. In addition, the prebiotic composition with the best effect of increasing the bacterial count of *Akkermansia muciniphila* was the prebiotic composition D composed of grape ferment, lactitol, and fructooligosaccharide.

Based on this, when the prebiotic composition is composed of the grape ferment, the lactitol, or the xylooligosaccharide as the first component, and the fructooligosaccharide, the xylooligosaccharide or the inulin as the second component, this prebiotic composition can promote growth of probiotics (such as *Akkermansia muciniphila*), thereby increasing the bacterial count of the probiotics.

Example 3: Effects of Prebiotic Compositions with Components in Different Ratios on Probiotics The components of the prebiotic composition used were the grape ferment prepared in Example 1, lactitol (purchased from Welltech Biotechnology Co., Ltd.) and fructooligosaccharide (purchased from Meiji). The liquid medium used was tryptone soy broth (TSB; hereinafter referred to as TSB medium) with 5% sheep blood (purchased from BD).

The groups were divided into blank group and 4 experimental groups (experimental groups A-D), as shown in Table 2.

TABLE 2

| Group | Components of medium | Ratio of components in prebiotic composition | | |
|---|---|---|---|---|
| | | Grape ferment | Lactitol | Fructooligo-saccharide |
| Blank group | 95% TSB medium + 5% sheep blood | — | — | — |
| Experimental group A | 94% TSB medium + 5% sheep blood + 1% prebiotic composition a | 34% | 33% | 33% |
| Experimental group B | 94% TSB medium + 5% sheep blood + 1% prebiotic composition b | 50% | 25% | 25% |
| Experimental group C | 94% TSB medium + 5% sheep blood + 1% prebiotic composition c | 25% | 50% | 25% |
| Experimental group D | 94% TSB medium + 5% sheep blood + 1% prebiotic composition d | 25% | 25% | 50% |
| Control group | 95% TSB medium + 5% sheep blood | | None | |

As shown in the table above, the weight ratio of the grape ferment, lactitol, and fructooligosaccharide in the prebiotic composition a was 1:1:1, the weight ratio of the grape ferment, lactitol, and fructooligosaccharide in the prebiotic composition b was 2:1:1, the weight ratio of the grape ferment, lactitol, and fructooligosaccharide in the prebiotic composition c was 1:2:1, and the weight ratio of the grape ferment, lactitol, and fructooligosaccharide in the prebiotic composition d was 1:1:2.

1% activated *Akkermansia muciniphila* was respectively added to a 15 mL test tube containing 5 mL of medium of each group, and subjected to anaerobic culture at 37° C. for 48 hours. After 48 hours of culture, 100 μL of bacterial suspension of each group was respectively taken from the test tube of each group, added to the solid TSB medium containing 5% sheep blood, and subjected to anaerobic culture at 37° C. for 72 hours, and then, the bacterial count of each group was calculated. The bacterial count was expressed by colony-forming unit.

Figure 2:
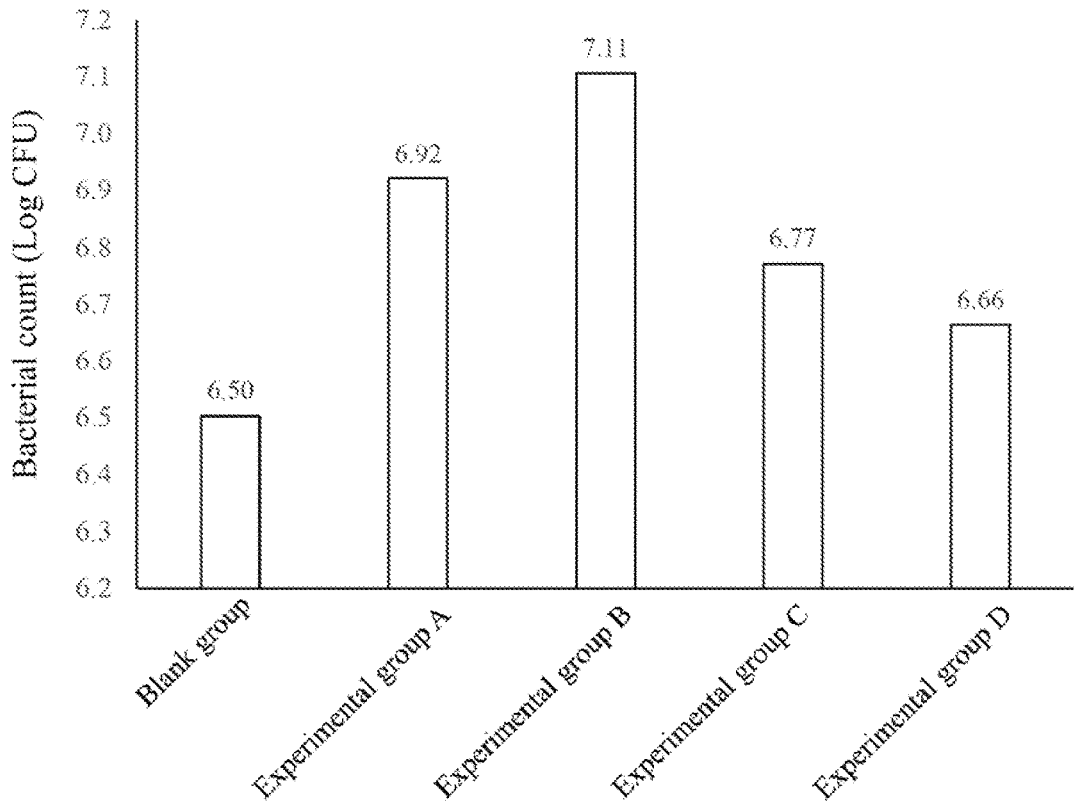
FIG. 2 is a graph showing experimental results of analysis on the effects of prebiotic compositions with components in different ratios on probiotics in multiple groups.

Referring to FIG. 2, the bacterial count of the blank group was 6.50 log CFU, the bacterial count of experimental group A was 6.92 log CFU, the bacterial count of experimental group B was 7.11 log CFU, the bacterial count of experimental group C was 6.77 log CFU, and the bacterial count of experimental group D was 6.66 log CFU.

As shown in FIG. 2, as compared with the blank group, the prebiotic compositions a-d including the grape ferment, lactitol, and fructooligosaccharide effectively promoted the growth of *Akkermansia muciniphila* and increase the bacterial count of *Akkermansia muciniphila*. In addition, when the prebiotic composition was composed of 50% grape ferment, 25% lactitol and 25% fructooligosaccharide, this prebiotic composition significantly promoted the growth of *Akkermansia muciniphila* by at least 1.1 folds.

Based on this, the prebiotic composition composed of the grape ferment, lactitol, and fructooligosaccharide in any ratio can effectively enhance the growth of probiotics (such as *Akkermansia muciniphila*). As compared with the other ratios, when the ratio of the grape ferment, lactitol, and fructooligosaccharide is 2:1:1, the prebiotic composition has significantly better effects of enhancing the growth of probiotics (such as *Akkermansia muciniphila*).

Example 4: Experiment on the Human Body 4-1. Experimental Design

Each capsule containing 400 mg of the prebiotic composition, composed of the grape ferment prepared in Example 1, lactitol (purchased from Welltech Biotechnology Co., Ltd.) and fructooligosaccharide (purchased from Meiji) in a weight ratio of 2:1:1, was provided to 7 subjects, one capsule per person per day, for 2 consecutive weeks. In other words, the daily dose per person was 400 mg of the prebiotic composition. In addition, every subject was tested at week 0 (before taking the prebiotic composition) and week 2 (2 weeks after taking the prebiotic composition).

4-2. Analysis of Intestinal Microbiota of Subjects

Feces of the 7 subjects were respectively collected before taking the prebiotic composition (i.e. at week 0) and after taking the prebiotic composition (i.e. at week 2), and BIOTOOLS was commissioned to conduct NGS analysis of fecal microbiota (sequencing position: 16S rRNA V3-V4) to determine the growth of the intestinal microbiota.

The strains for analyzing the microbiota were *Akkermansia muciniphila* (hereinafter referred to as AKK) and *Bifidobacterium*.

Figure 3:
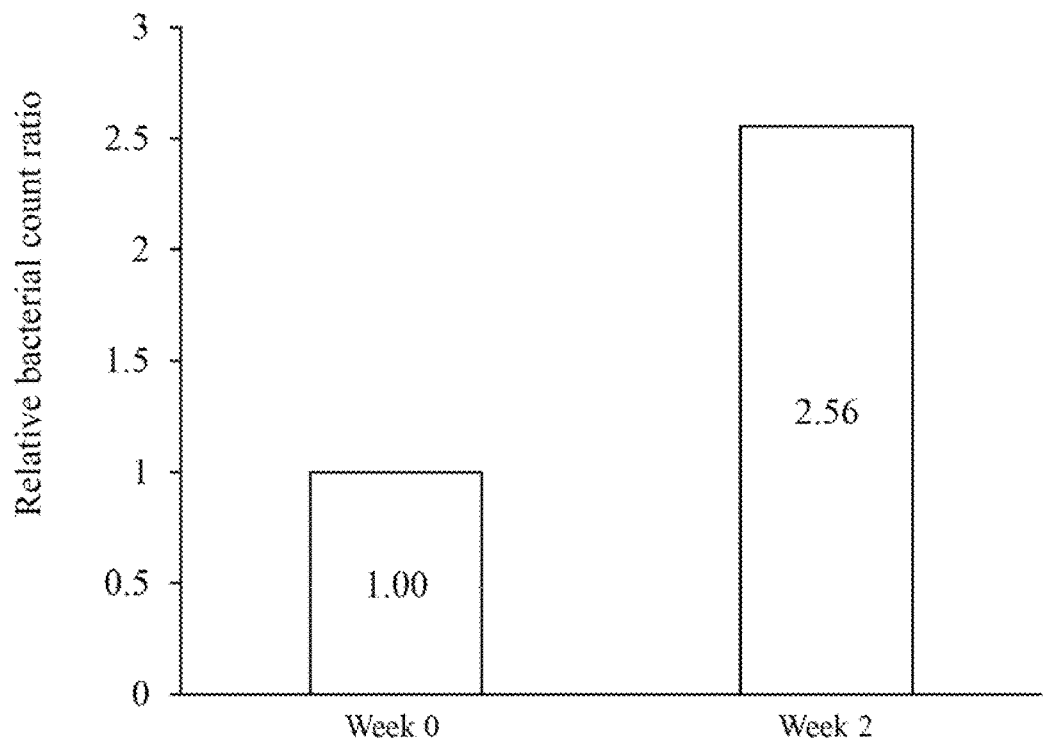
FIG. 3 is a graph showing experimental results of analysis on the effects of the prebiotic composition on growth of *Akkermansia muciniphila*.

Referring to FIG. 3, the average AKK bacterial count of the 7 subjects at week 0 was regarded as 1, and the average AKK bacterial count ratio of the 7 subjects at week 2 was calculated based on this. The average AKK bacterial count ratio of the 7 subjects at week 2 was 2.56. That is, after the 7 subjects took the prebiotic composition for 2 consecutive weeks, the bacterial count of AKK in the intestinal tract was increased by 2.56 folds, and the metabolites of AKK suppressed the appetite of the host and induced the expression of FIAF (fasting-induced adipose factor) gene of the host, thereby lowering the ability of the host to store fat. In addition, the increase of the bacterial count of AKK in the intestinal tract reversed high-fat diet-induced obesity and reduced the lipopolysaccharide concentration of harmful bacteria in blood, thereby reducing chronic inflammation and lowering insulin resistance. Therefore, by taking the prebiotic composition composed of grape ferment, lactitol, and fructooligosaccharide, the bacterial count of AKK in the intestinal tract of the user can be effectively increased, thereby achieving the effects of reducing weight, reducing chronic inflammation, lowering insulin resistance and the like.

Figure 4:
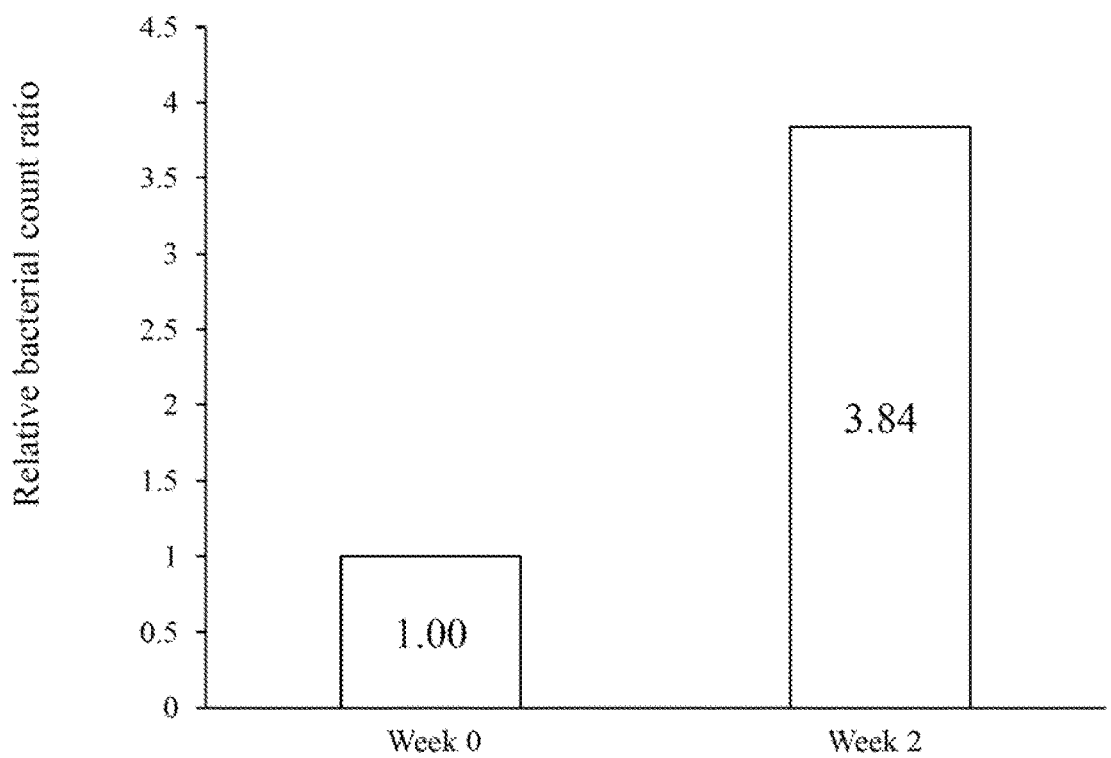
FIG. 4 is a graph showing experimental results of analysis on the effects of the prebiotic composition on growth of *Bifidobacterium*.

Referring to FIG. 4, the average *Bifidobacterium* bacterial count of the 7 subjects at week 0 was regarded as 1, and the average *Bifidobacierium* bacterial count ratio of the 7 subjects at week 2 was calculated based on this. The average *Bifidobacterium* bacterial count ratio of the 7 subjects at week 2 was 3.84. That is, after the 7 subjects took the prebiotic composition for 2 consecutive weeks, the bacterial count of AKK in the intestinal tract was increased by 3.84 folds. In addition, when the bacterial count of *Bifidobacterium* in the human intestinal tract increased, the *Bifidobacterium*, as a physiologically beneficial bacterium, improved the biological barrier of the human body, provided nutrition to the human body, enhanced the immunity of the human body, improved the gastrointestinal health of the human body and enhanced the anti-aging ability of the human body, thereby making the human body healthy. Therefore, by taking the prebiotic composition composed of grape ferment, lactitol, and fructooligosaccharide, the bacterial count of *Bifidobacterium* in the intestinal tract of the user can be effectively increased, thereby increasing the bacterial count of the probiotics in the intestinal tract of the subject, and achieving the physiological functions beneficial to health, such as improving the biological barrier of the subject, providing nutrition to the subject, enhancing the immunity of the subject, improving the gastrointestinal health of the subject and enhancing the anti-aging ability of the subject.

4-3. Analysis of CLDN3 Protein Content in Blood of Subjects 6 mL of venous blood of the 7 subjects was respectively collected using a purple cap blood collection tube containing EDTA anticoagulant before taking the prebiotic composition (i.e. at week 0) and after taking the prebiotic composition (i.e. at week 2), and TCI GENE was commissioned to conduct expression level analysis of sulfur compounds and total glutathione (t-GSH) in the blood. The test sulfur compounds were f-thiols. f-thiols and total glutathione are indicators of antioxidation in the human body. The increase in the content of the f-thiols or glutathione indicates the increase in the ability of scavenging free radicals in the body, so that the defense against oxidative stress on cells is enhanced.

Figure 5:
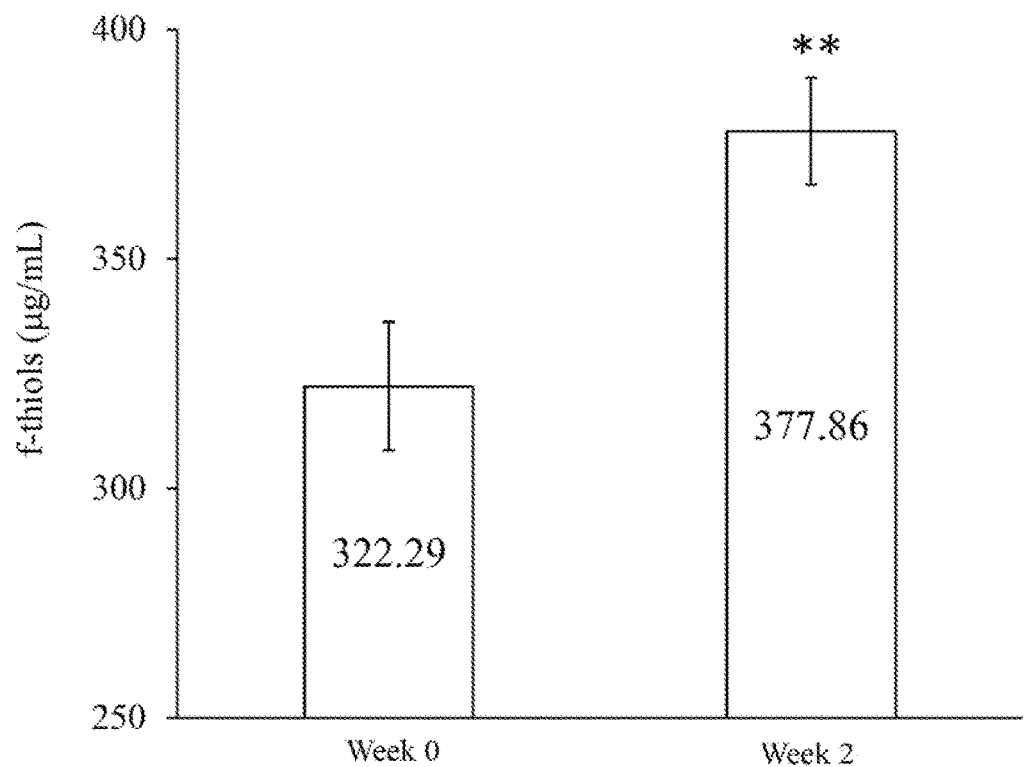
FIG. 5 is a graph showing results of analysis on the effects of the prebiotic composition on the content of f-thiols in blood of a subject.

Referring to FIG. 5, the average f-thiols content in the blood of the 7 subjects at week 0 was 322.29 µg/mL, and the average f-thiols content in the blood after taking the prebiotic composition for 2 weeks was increased to 377.86 µg/mL. That is, after taking the prebiotic composition for 2 weeks, the average f-thiols content in the blood increased by 55.57 µg/mL (equivalent to an increase of 17.2%). Therefore, by taking the prebiotic composition, the content of f-thiols can be effectively increased, thereby enhancing the ability of scavenging free radicals in the body, and enhancing the antioxidant capacity.

Figure 6:
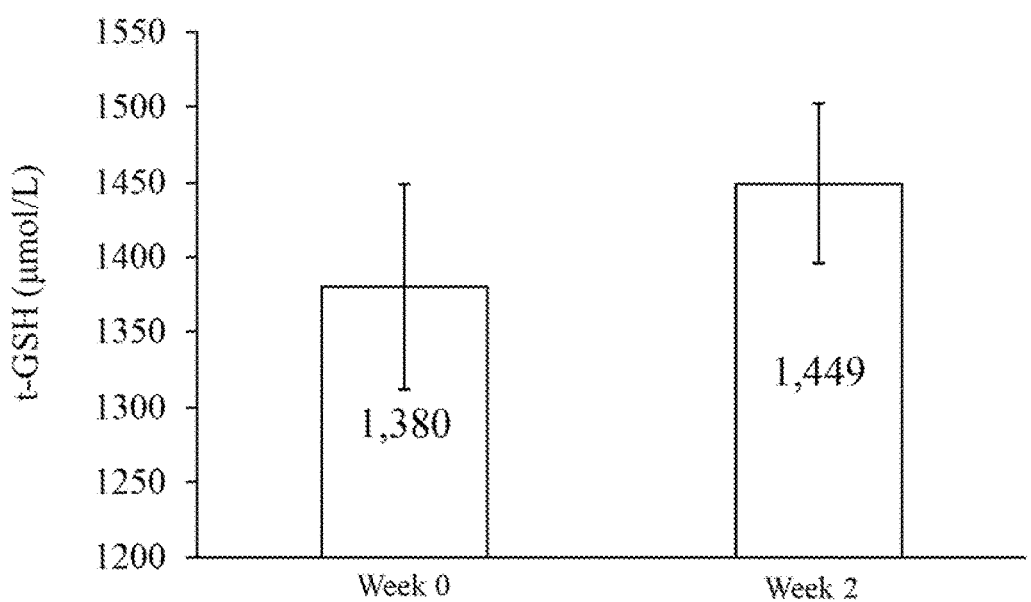
FIG. 6 is a graph showing results of analysis on the effects of the prebiotic composition on the content of t-GSH in blood of a subject.

Referring to FIG. 6, the average total glutathione content in the blood of the 7 subjects at week 0 was 1380 µmol/L, and the average total glutathione content in the blood after taking the prebiotic composition for 2 weeks was increased to 1449 µmon. That is, after taking the prebiotic composition for 2 weeks, the average total glutathione content in the blood increased by 69 µmol/L (equivalent to an increase of 5%). Therefore, by taking the prebiotic composition, the content of total glutathione can be effectively increased, thereby enhancing the ability of scavenging free radicals in the body, and enhancing the antioxidant capacity.

Based on the above, the prebiotic composition prepared based on the grape ferment according to any embodiment of the present invention can be used to promote growth of *Akkermansia muciniphila*. The prebiotic composition includes the grape ferment, the lactitol, or the xylooligosaccharide as the first component, and the fructooligosaccharide, the xylooligosaccharide, or the inulin as the second component, and the weight ratio of the grape ferment, the first component and the second component falls within a range of 1-2:1-2:1-2. In some embodiments, the prebiotic composition prepared from the grape ferment, lactitol, and fructooligosaccharide can be used to promote intestinal health of the subject and/or enhance antioxidation in the subject. The weight ratio of the grape ferment, lactitol, and fructooligosaccharide included in the prebiotic composition falls within a range of 1-2:1-2:1-2. In some embodiments, the prebiotic composition can promote intestinal health of the subject by promoting growth of the probiotics (such as *Akkermansia muciniphila* and *Bifidobacterium*). In some embodiments, the prebiotic composition can enhance antioxidation in the subject by increasing the contents of sulfur compounds (such as thiols) and total glutathione in the subject.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A prebiotic composition, comprising:
   grape ferment;
   a first component, wherein the first component comprises lactitol or xylooligosaccharide; and
   a second component, wherein the second component comprises fructooligosaccharide, xylooligosaccharide, or inulin;
   wherein the first component is different from the second component;
   wherein a weight ratio of the grape ferment, the first component and the second component falls within a range of 1-2:1-2:1-2,
   wherein the grape ferment is obtained by following steps:
   blending concentrated juice of red grapes (*Vitis vinifera*) and water in 1:8 volume ratios to obtain a grape juice solution;
   treating the grape juice solution added 3% (W/V) glucose at 95° C. for 0.5 hour to obtain a grape extract;
   fermenting the grape extract with 0.1% (W/V) *Saccharomyces cerevisiae* and 0.05% (W/V) *Streptococcus thermophilus* at 30° C. for 72 hours to obtain a grape fermentation primary solution; and
   concentrating the grape fermentation primary solution at 60° C. and filtering the concentrated grape fermentation primary solution through a filter screen with a pore size of 400 mesh to obtain the grape ferment.

2. The prebiotic composition according to claim 1, wherein the weight ratio of the grape ferment, the first component and the second component is 2:1:1.

3. The prebiotic composition according to claim 1, wherein the first component is the lactitol, and the second component is the fructooligosaccharide.

4. The prebiotic composition according to claim 1, wherein the prebiotic composition is used to promote growth of *Akkermansia muciniphila*.

* * * * *